United States Patent [19]

Imahori et al.

[11] 4,282,352

[45] Aug. 4, 1981

[54] ADENOSINE TRIPHOSPHATE DERIVATIVE

[75] Inventors: Kazutomo Imahori, Tokyo; Kosuke Tomita, Matsudo, both of Japan

[73] Assignee: Unitika Ltd., Amagasaki, Japan

[21] Appl. No.: 91,996

[22] Filed: Nov. 7, 1979

[30] Foreign Application Priority Data

Nov. 8, 1978 [JP] Japan ................................. 53/138123

[51] Int. Cl.³ ............................................. C07H 17/00
[52] U.S. Cl. .......................................... 536/27; 536/28
[58] Field of Search ............................... 536/28, 27, 26

[56] References Cited

PUBLICATIONS

Mosbach, European Journal of Biochemistry, vol. 53, p. 481 (1975).

*Primary Examiner*—Johnnie R. Brown
*Assistant Examiner*—Blondel Hazel

*Attorney, Agent, or Firm*—Sughrue, Rothwell, Mion, Zinn and Macpeak

[57] ABSTRACT

An adenosine triphosphate derivative represented by the formula:

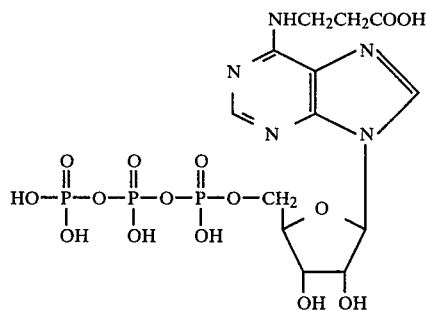

and salts thereof.

3 Claims, No Drawings

ADENOSINE TRIPHOSPHATE DERIVATIVE

BACKGROUND OF THE INVENTION

1. Field of the Invention

The present invention relates to a novel adenosine triphosphate derivative and, more particularly, to an adenosine triphosphate derivative useful as a ligand for affinity chromatography or as an enzyme auxiliary substrate (cofactor) in industrial enzyme applications.

2. Description of the Prior Art

Affinity chromatography has been studied recently as an effective means for isolating biological materials. Adenosine triphosphate (ATP) is a very important cofactor for enzyme reactions. Accordingly, when a material prepared by fixing ATP to a suitable matrix is used as an affinity adsorbent, it becomes possible to isolate and purify enzymes by affinity chromatography. Further, in case of many a chemical reaction utilizing an enzyme system in combination with a cofactor such as ATP on an industrial scale, it is very important to be able to smoothly carry out the mutual conversion of ATP and adenosine diphosphate (ADP), and separation of the cofactor from by-products is required. It is generally recognized that supporting the cofactor on a suitable matrix is the best method of facilitating separation.

Accordingly, there are many instances in which it is necessary to attach the ATP to a suitable matrix. However, it is difficult to attach the ATP itself to the matrix and it is thus necessary to introduce functional groups into the ATP which can be easily linked to a matrix.

ATP derivatives generally have a low substrate activity as compared with ATP. Accordingly, it has been desired to find ATP derivatives having a higher substrate activity.

$N^6$-(carboxymethyl) ATP produced by Mosbach, *European Journal of Biochemistry*, Vol. 53, (1975), page 481 and $N^6$-[N-(6-aminohexyl)carbamoyl] ATP produced by Yamazaki et al, *European Journal of Biochemistry*, Vol. 77, (1977), page 511 are two ATP derivatives. Hitherto, it has been known that when a functional group is introduced into a position other than the $N^6$-position of ATP very low substrate activity is obtained. While both of the aforementioned compounds bear the functional group at the $N^6$-position, these compounds do not have a very high substrate activity and problems arise on their practical use. Because the $N^6$-carboxymethyl compound is chemically unstable, side reactions occur when counting to a matrix or introduction of a spacer is carried out by reacting the $N^6$-carboxyl group with an amino group containing compound and, consequently, it is very difficult to accomplish the desired reaction. On the other hand, the latter compound is synthesized from ADP which is much more expensive than ATP.

SUMMARY OF THE INVENTION

It has been found that an ATP derivative represented by the following formula has excellent substrate activity and practicability as compared with the prior ATP derivatives.

Namely, the object of the present invention is to provide an ATP derivative represented by the formula:

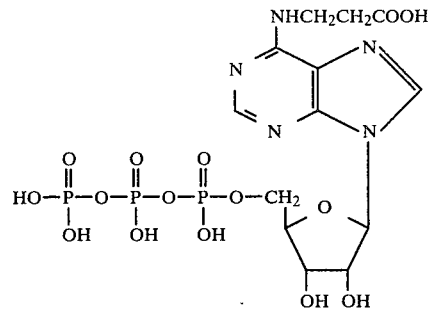

The ATP derivative of the present invention also includes salts thereof such as alkali metal salts wherein one or more of the phosphates or carboxyl groups is substituted with an alkali metal atom.

DETAILED DESCRIPTION OF THE INVENTION

The ATP derivative of the present invention can be synthesized by various processes. For example, it is easily synthesized by reacting ATP dissolved in water with β-halopropionic acid such as β-iodopropionic acid or β-bromopropionic acid or β-propiolactone and carrying out a Dimroth rearrangement of the resulting 1-(carboxyethyl) ATP. The derivative in a free acid form is neutralized, if desired, with a base to form the corresponding salt. In water, ATP is reacted with β-halopropionic acid or β-propiolactone at a pH of about 5 to 8, preferably about 6 to 7 at about 20° to 50° C. The acid and lactone are used in amounts at least equimolar to, preferably 5 times or more, the amount of ATP. The Dimroth rearrangement, this reaction is preferably carried out at a pH of 8 to 11, more preferably about 9, at 60° to about 90° C. Reference can be made to Mosbach, above.

The ATP derivative of the present invention has a carboxyl group as a functional group at the $N^6$-position and can be referred to as $N^6$-(carboxyethyl) ATP. Accordingly, it is structurally similar to $N^6$-(carboxymethyl) ATP described above. However, by comparison of them, the ATP derivative of the present invention has a higher substrate activity and the drawbacks of the carboxymethyl derivative are not observed upon reaction with an amino group-containing compound as a matrix or a spacer.

The ATP derivative of the present invention can be applied to most enzymes for which an adenine nucleotide is a substrate or a coenzyme. $N^6$-(carboxyethyl) ATP of the present invention can react with an amino group-containing compound as a matrix or a spacer and be coupled thereto, as described above.

Examples of amino group-containing compounds with which react the derivative of the present invention include aminoalkyl agaroses such as agarose aminohexane, aminoalkyl celluloses such as aminohexyl cellulose, polylysine, polyethyleneimine (the above-described compounds are matrices) and alkylenediamines such as hexamethylenediamine (spacer).

The ATP derivative of the present invention can be applied to enzymes such as kinases and dehydrogenases. Particularly, the industrial utility of acetate kinase has been widely studied as an enzyme for mutual conversion of adenine cofactor such as ATP and ADP. The acetate kinase is superior to other kinases in that the mutual conversion ratio of ATP and ADP (ATP- ⇌ADP) is high and the acetyl phosphate of the phosphate donor can be easily synthesized (ATP+acetic acid⇌ADP+acetyl phosphate).

In the following, examples of the present invention are described. However, the present invention is not of course limited to these examples.

EXAMPLE 1

1 g of disodium ATP was dissolved in 10 ml of water. After adding 5 g of β-iodopropionic acid thereto, the pH was adjusted to 6.5 and the reaction was carried out at room temperature. During the reaction, the pH was kept at 6.5 with a 2 M lithium hydroxide. After 8 days, 10 volumes of an acetone-ethanol mixture (1:1, ratio by volume) was added to the reaction mixture. The precipitate was collected, washed with the above described acetone-ethanol mixture and the acetone-ethanol mixture was then removed under reduced pressure. The yield was 1.17 g. After the precipitate was dissolved in 10 ml of water, the pH was adjusted to 8.5 and the rearrangement was carried out at 70° C. During the reaction, the pH was kept at 8.5 with 2 M lithium hydroxide. After 2.5 hours, the solution containing the rearranged compound was cooled with ice, adjusted to pH 7 with 1 N hydrochloric acid, and applied to a Dowex 1-X8 column (Cl⁻ type, 200–400 mesh, 2 cm in diameter and 32 cm long). The column was first washed with 300 ml of water, and a linear lithium chloride gradient was applied: the mixing chamber contained 500 ml of 0.3 M lithium chloride and the reservoir 500 ml of 0.5 M lithium chloride. In the effluent, principal fractions having a U.V. absorption at 268 nm were collected and concentrated. An ethanol-acetone solvent mixture (1:1, ratio by volume) was added to obtain 0.39 g of $N^6$-(carboxyethyl) ATP as a white powder.

When this product was analyzed by cellulose thin layer chromatography (Avicel-SF) using a 0.1 M potassium phosphate (pH: 6.8):ammonium sulfate:1-propanol mixture in a ratio of 100 (v):60 (w):2 (v) as a developer solvent, a single spot was obtained at Rf 0.42. The ultraviolet absorption spectrum showed a λmax 268 nm ($\epsilon = 15500$ $M^{-1}cm^{-1}$) in an aqueous solution having pH 7.

Further, the structure of the compound was ascertained by proton nuclear magnetic resonance (NMR) in heavy water. The NMR spectrum was characterized by the absorptions of the two hydrogen atoms on the purine ring at $\delta = 8.86$ and 8.65 (singlet, respectively), the absorption of the hydrogen atom at the 1'-position of ribose at $\delta = 6.56$ (doublet) and the absorptions of the hydrogen atoms on the ethylene of the carboxyethyl group at $\delta = 4.20$ and 3.02 (triplet, respectively).

Further, it was ascertained by color formation in molybdenum blue reaction that the compound had three phosphorus atoms.

EXAMPLE 2

1 g of disodium ATP was dissolved in 10 ml of water and 0.6 ml of β-propiolactone was added thereto at pH 6.8. The reaction was carried out at room temperature at a pH of 6.8 with a 2 M lithium hydroxide. After 56 hours, 10 volumes of an acetone-ethanol mixture (1:1, ratio by volume) was added thereto to precipitate the product. The product was subjected to rearrangement at 70° C. and pH 8.5 in the same manner as in Example 1 and separated by Dowex 1-X8 column to obtain 0.20 g of $N^6$-(carboxyethyl) ATP. When it was analyzed in the same manner as in Example 1, it was ascertained that the compound had the same structure as that in Example 1.

REFERENCE EXAMPLE 1

$N^6$-(carboxymethyl) ATP and $N^6$-[N-(6-aminohexyl)-carbamoyl] ATP were synthesized according to Mosbach et al and Yamazaki et al, and a substrate activity of each was compared with that of the ATP derivative of the present invention obtained in Example 1. Substrate activity was tested as described in *Biochemica Information*, Boehringer Mannheim Co (1973) using, as the enzyme, acetate kinase from Bacillus stearothermophilus (prepared by the process described in Japanese Patent Application (OPI) No. 25088/77 (The term "OPI" as used herein refers to a "published unexamined Japanese patent application")) in specific activity of 1360 units/mg. The change in absorbance at 340 nm per time was measured by the same manner except that 2 mM of fructose 1,6-diphosphate was added to the assay mixture. The respective maximum reaction velocities (V max) are set forth below based on ATP as 100.

$N^6$-(carboxyethyl) ATP (invention) 35
$N^6$-(carboxymethyl) ATP 20
$N^6$-[N-(6-aminohexyl)carbamoyl] ATP 23

The results demonstrate the higher substrate activity of the derivative of the present invention.

REFERENCE EXAMPLE 2

After 100 mg of each of $N^6$-(carboxymethyl) and $N^6$-(carboxyethyl) ATP derivatives was dissolved in 5 ml of water, 400 mg of hexamethylenediamine was added. While keeping the pH at 4.7 using 0.5 M HCl, 150 mg of 1-ethyl-3-(3-dimethylaminopropyl)carbodiimide hydrochloride (EDC) was added thereto in a conventional manner to compare the abilities of the derivatives to react with this conventional spacer. In the case of $N^6$-(carboxymethyl) ATP, the reaction solution yellowed within several minutes and gradually changed to a red color and became viscous. When recovery of the reaction product in this state was attempted using various nonsolvents, the reaction product did not crystallize and could not be obtained.

On the other hand, with the ATP derivative of the present invention, such a disadvantageous phenomenon was not observed and a crude reaction product was obtained as a white powder by adding 10 volumes of the acetone-ethanol mixture (1:1, ratio by volume) to the reaction mixture. The yield after 4 horus was 90 mg in case of EDC for the derivative of the present invention.

While the invention has been described in detail and with reference to specific embodiments thereof, it will be apparent to one skilled in the art that various changes and modifications can be made therein without departing from the spirit and scope thereof.

What is claimed is:

1. An adenosine triphosphate derivative represented by the formula:

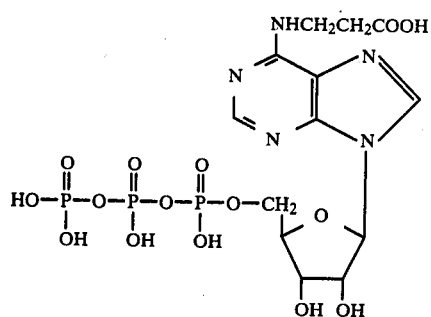
and alkali metal salts thereof.
* * * * *